(12) United States Patent
Frushour et al.

(10) Patent No.: US 9,472,966 B2
(45) Date of Patent: Oct. 18, 2016

(54) SURGICAL TRAY ASSEMBLIES FOR STORING, CHARGING, POWERING, AND/OR COMMUNICATING WITH SURGICAL INSTRUMENTS

(71) Applicant: COVIDIEN LP, Mansfield, MA (US)

(72) Inventors: Scott E. M. Frushour, Boulder, CO (US); Robert B. Stoddard, Steamboat Springs, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/602,444

(22) Filed: Jan. 22, 2015

(65) Prior Publication Data
US 2015/0366617 A1 Dec. 24, 2015

Related U.S. Application Data

(60) Provisional application No. 62/014,358, filed on Jun. 19, 2014.

(51) Int. Cl.
*B62B 3/00* (2006.01)
*H02J 7/00* (2006.01)
*H02J 7/02* (2016.01)
*A61B 17/00* (2006.01)

(52) U.S. Cl.
CPC .............. *H02J 7/0045* (2013.01); *A61B 50/13* (2016.02); *A61B 50/20* (2016.02); *A61B 50/24* (2016.02); *A61B 50/33* (2016.02); *H02J 7/0052* (2013.01); *H02J 7/025* (2013.01); *A61B 2017/00221* (2013.01); *A61B 2050/155* (2016.02); *A61B 2560/0214* (2013.01)

(58) Field of Classification Search
CPC .......... A61B 19/0271; A61B 19/0256; A61B 50/13; A61B 50/20; A61B 50/24; B62B 3/00
USPC ....................................... 280/47.35
See application file for complete search history.

(56) References Cited

U.S. PATENT DOCUMENTS

| | | | |
|---|---|---|---|
| 5,399,007 A * | 3/1995 | Marconet | A61B 19/0248 312/209 |
| 5,518,310 A | 5/1996 | Ellman et al. | |
| 5,536,084 A | 7/1996 | Curtis et al. | |
| 6,315,308 B1 | 11/2001 | Konopka | |
| 6,493,220 B1 * | 12/2002 | Clark | A47B 21/00 248/918 |
| 6,626,445 B2 | 9/2003 | Murphy et al. | |
| 6,746,091 B2 | 6/2004 | Friar et al. | |
| 6,831,225 B2 | 12/2004 | Chandler | |
| 6,876,902 B2 | 4/2005 | Nikolich | |
| 7,009,840 B2 | 3/2006 | Clark et al. | |
| 7,581,708 B2 | 9/2009 | Newkirk | |

(Continued)

*Primary Examiner* — Hau Phan

(57) ABSTRACT

A surgical tray assembly for storing, charging, and/or communicating with battery powered surgical instruments and other communication-enabled devices. The surgical tray assembly includes a stand, a surgical instrument tray supported on the stand, an electrical connector coupled to the tray, and one or more electrical transmission devices. The electrical connector is configured to be inserted into an electrical outlet. The electrical transmission device(s) is in electrical communication with the electrical connector. The surgical tray assembly may further include a wireless communication system capable of capturing data from a battery powered surgical instrument and transmitting such data. The surgical tray may further include a user interface display for displaying captured data from a battery powered surgical instrument.

20 Claims, 3 Drawing Sheets

(56) References Cited

U.S. PATENT DOCUMENTS

| | | | |
|---|---|---|---|
| 7,612,999 B2 * | 11/2009 | Clark | A61B 5/0002 248/918 |
| 7,800,914 B2 | 9/2010 | Dully | |
| 7,806,376 B2 | 10/2010 | Song et al. | |
| 7,809,470 B2 | 10/2010 | Shoenfeld | |
| 8,106,746 B2 | 1/2012 | Maltseff et al. | |
| 8,109,527 B2 | 2/2012 | Bustle et al. | |
| 8,180,485 B2 * | 5/2012 | Reckelhoff | A61G 12/001 700/237 |
| 8,210,548 B1 | 7/2012 | Agyemang | |
| 8,215,650 B2 | 7/2012 | Arceta et al. | |
| 8,258,973 B2 | 9/2012 | Newkirk | |
| 8,286,977 B2 | 10/2012 | Butler et al. | |
| 8,287,816 B2 | 10/2012 | Kral | |
| 8,295,940 B2 | 10/2012 | Sherman | |
| 8,398,408 B1 * | 3/2013 | Hansen | A61B 8/4433 320/109 |
| 8,775,828 B2 * | 7/2014 | Coonan | A61B 5/7475 713/300 |
| 8,812,153 B2 * | 8/2014 | Reckelhoff | A61G 12/001 700/237 |
| 9,039,016 B2 * | 5/2015 | Abernethy | B62B 3/02 280/6.15 |
| 9,139,213 B2 * | 9/2015 | Trish | A61G 12/001 |
| 2002/0013640 A1 | 1/2002 | Phoon et al. | |
| 2003/0201697 A1 | 10/2003 | Richardson | |
| 2005/0178298 A1 | 8/2005 | Rossini | |
| 2005/0236940 A1 | 10/2005 | Rockoff | |
| 2007/0018433 A1 | 1/2007 | Sinnamon et al. | |
| 2008/0203861 A1 | 8/2008 | Wingate | |
| 2008/0303389 A1 | 12/2008 | Petrovich | |
| 2008/0316045 A1 | 12/2008 | Sriharto et al. | |
| 2009/0261992 A1 | 10/2009 | Song | |
| 2009/0267772 A1 | 10/2009 | Dehnadi | |
| 2010/0174415 A1 * | 7/2010 | Humayun | A61B 19/0271 700/282 |
| 2010/0213679 A1 | 8/2010 | Smith et al. | |
| 2010/0264738 A1 | 10/2010 | Murtha et al. | |
| 2011/0172815 A1 | 7/2011 | Kim | |
| 2015/0148615 A1 * | 5/2015 | Brennan | A61F 9/00736 600/249 |

* cited by examiner

SURGICAL TRAY ASSEMBLIES FOR STORING, CHARGING, POWERING, AND/OR COMMUNICATING WITH SURGICAL INSTRUMENTS

CROSS REFERENCE TO RELATED APPLICATION

The present application claims the benefit of and priority to U.S. Provisional Application Ser. No. 62/014,358, filed on Jun. 19, 2014, the entire contents of which are incorporated herein by reference.

BACKGROUND

1. Technical Field

The present disclosure relates generally to operating room equipment, and in particular, to portable surgical tray assemblies for storing, charging, powering, and/or communicating with powered surgical instruments.

2. Background of the Disclosure

Portable surgical trays, referred to as "mayo stands," are commonly used in operating rooms throughout the world. Mayo stands provide a sterile, easily maneuverable platform on which surgeons may place various surgical instruments during a surgical procedure. Despite all these attributes, typical mayo stands are limited in their ability to accommodate and facilitate the use of battery-powered surgical instruments, which are becoming increasingly prevalent within operating rooms.

Battery-powered surgical instruments are advantageous in that they reduce the numbers of cables, cords, and/or wires in the operating room and are freely movable without tangling and/or cable-length restrictions. However, batteries typically provide adequate power for only a finite period of time. This attribute limits the ability of the surgeon to enjoy continued use of the battery-powered instrument during long surgical procedures without frequent battery changes; a time consuming process that frequently requires removal of the battery from the sterile field for charging and re-sterilization before the battery can again be utilized.

SUMMARY

The present disclosure is directed to a surgical tray assembly for storing, charging, and/or communicating with battery powered surgical instruments and/or other communication-enabled components utilized within or outside the operating room. The surgical tray assembly includes a stand, a surgical instrument tray supported on the stand, one or more electrical connectors coupled to the stand, and one or more electrical transmission devices disposed on the surgical instrument tray. The electrical connector is configured to be inserted into an electrical outlet and the electrical transmission device is in electrical communication with the electrical connector, e.g., so as to be powered from the electrical outlet.

In aspects of the present disclosure, the surgical tray assembly includes a base member, one or more legs extending from the base member, one or more caster wheels coupled to the base member, one or more support tubes extending from an upper side of the base member, an elongate body coupled to an upper end of the support tube, and one or more tray supports extending from a side of the elongate body. The surgical instrument tray is disposed on an upper side of the tray support(s).

In aspects of the present disclosure, the surgical tray assembly includes one or more batteries disposed thereon, e.g., on the base member thereof, in electrical communication with the one or more electrical transmission devices. The batteries may be provided in addition to (e.g., in electrical communication with), or in place of, the electrical connector.

In aspects of the present disclosure, one or more of the electrical transmission devices is a physical contact battery charger. One or more of the electrical transmission devices may alternatively or additionally be a wireless charging apparatus.

In aspects of the present disclosure, the surgical tray assembly further includes a wireless communication system. The wireless communication system may be configured to wirelessly communicate with one or more battery powered surgical instruments (or other communication-enabled devices) and capture data therefrom.

In aspects of the present disclosure, the surgical tray assembly further includes a user interface display disposed thereon. The user interface display may be a touch screen.

In aspects of the present disclosure, the user interface display is configured to communicate with one or more battery powered surgical instruments (or other communication-enabled devices) to capture and display data therefrom.

Another surgical tray assembly provided in accordance with the present disclosure includes a stand and a surgical instrument tray supported on the stand. The stand includes a base member, an upper member, one or more support tubes extending between the base member and the upper member, and one or more tray supports coupled to the upper member and configured to support the surgical instrument tray. The surgical instrument tray includes one or more electrical transmission devices disposed thereon. An electrical power provider is coupled to the base member. The electrical transmission device is disposed in electrical communication with the electrical power provider via one or more cables routed through the base member, the upper member, and/or the support tube of the stand. The electrical power provider is configured to power the electrical transmission device(s).

In aspects of the present disclosure, the electrical power provider is an electrical connector configured to selectively engage a wall outlet thereby causing the electrical connector and wall outlet to be in electrical communication.

In aspects of the present disclosure, the electrical power provider includes one or more batteries seated on the base member of the stand.

In aspects of the present disclosure, one or more of the electrical transmission devices is a physical contact battery charger.

In aspects of the present disclosure, one or more of the electrical transmission devices is a wireless charging apparatus.

In aspects, the surgical tray assembly further includes a wireless communication system configured to wirelessly communicate with a battery powered surgical instrument to capture data from the battery powered surgical instrument.

In aspects of the present disclosure, the surgical tray assembly includes a user interface display disposed on the surgical instrument tray. The user interface display is configured to wirelessly communicate with a battery powered surgical instrument and is configured to capture and display data received therefrom.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Figure 1:
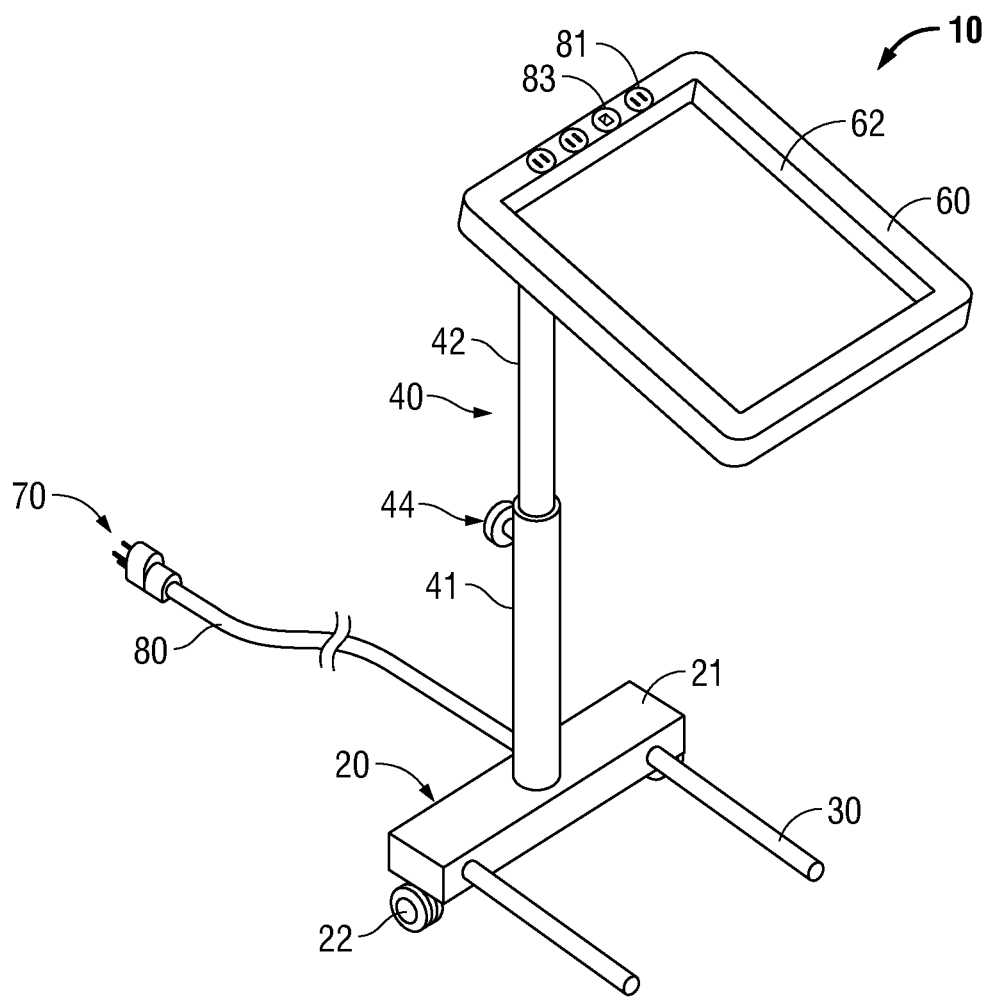
FIG. 1 is a perspective view from a first side of a surgical tray assembly provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
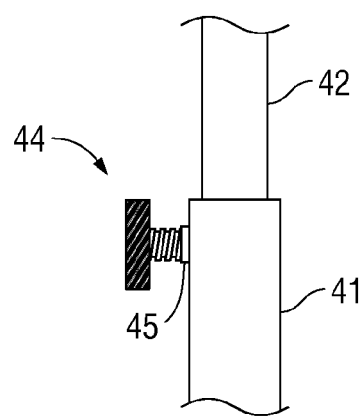
FIG. 2 is a side view of a locking assembly of the surgical tray assembly of FIG. 1.
Figure 3:
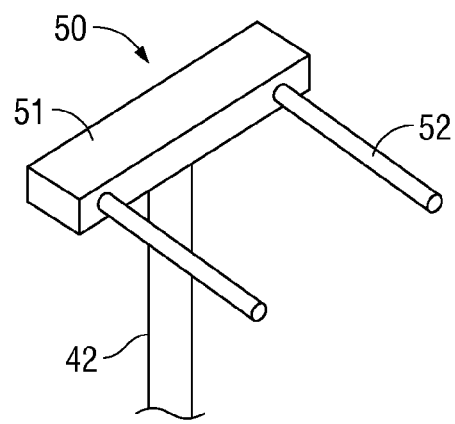
FIG. 3 is a perspective view of tray supports of the surgical tray assembly of FIG. 1.

FIGS. 1-3 illustrate a surgical tray assembly 10 provided in accordance with the present disclosure that generally includes a base member 20, one or more leg 30, a support post 40, tray supports 50 (FIG. 3), and a surgical tray 60.

Referring in particular to FIG. 1, base member 20 includes an elongate body 21 and may be constructed of any suitable material for use in an operating room, e.g., stainless steel. Base member 20 includes one or more caster wheels 22 affixed to an underside of elongate body 21 thereby permitting surgical tray assembly 10 to be selectively maneuvered by a clinician. The caster wheel(s) 22 may be any caster wheels suitable for use in an operating room. As illustrated in FIG. 1, two caster wheels 22, one at each end of elongated body 21, are provided, although other configurations are also contemplated.

The leg(s) 30 extends in a direction generally perpendicular from elongate body 21 and may be constructed from any suitable material for use in an operating room, e.g., stainless steel. The leg(s) 30 is rigidly secured to elongate body 21 thereby providing support to facilitate maintaining surgical tray assembly 10 in a vertical orientation. As illustrated in FIG. 1, two legs 30 extending from opposite ends of elongated body 21 are provided, although other configurations are also contemplated.

Support post 40 extends vertically from an upper side of elongate body 21 and may be constructed of any suitable material for use in an operating room, e.g., stainless steel. Support post 40 is rigidly affixed to elongate body 21 on a lower end. Support post 40 includes a lower portion 41 and upper portion 42 which are coupled to each other in a nested configuration wherein the upper portion 42 is slidably disposed within a longitudinal bore (not explicitly shown) defined within lower portion 41. With additional reference to FIG. 2, a locking assembly 44 is disposed at an upper end of lower portion 41 and is engaged within a threaded insert 45. A locking screw of the locking assembly 44 is configured to be loosened relative to threaded insert 45 to permit insertion and withdrawal of the upper portion 42 into and from lower portion 41, and tightened relative to threaded insert 45 to fix the position of the upper portion 42 relative to lower portion 41 thereby establishing a set height of tray supports 50. Other suitable locking assemblies and/or configurations may also be utilized to enable selective adjustment of the height of tray supports 50.

With reference to FIG. 3, tray support 50 is shown. Tray support 50 includes elongate body 51 extending in a direction generally parallel to elongate body 21 of base member 20. Elongate body 51 is rigidly affixed on an underside to upper portion 42 and may be constructed of any suitable material for use in an operating room, e.g., stainless steel. Alternatively, elongate body 51 may be pivotably coupled to upper portion 42 to permit tilting of tray support 50 relative to base member 20.

One or more arm(s) 52 extend in a direction generally perpendicular from a side of elongate body 51 and substantially parallel to the leg(s) 30 of base member 20. The arm(s) 52 may be constructed from any suitable material for use in an operating room, e.g., stainless steel. The arm(s) 52 is rigidly secured to elongate body 51 for supporting surgical tray 60, as detailed below. As illustrated in FIG. 3, two arms 52, one at each end of elongated body 51, are provided, although other configurations are also contemplated.

Figure 4:
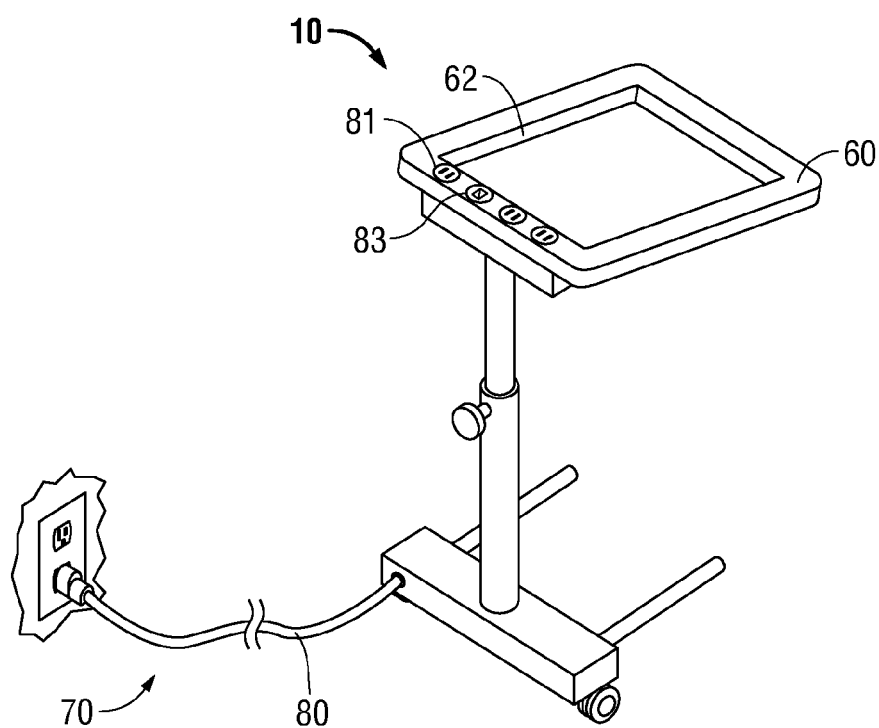
FIG. 4 is a perspective view from a second side of the surgical tray assembly of FIG. 1.

Referring to FIGS. 1 and 4, surgical tray 60 may be fixed to arm(s) 52 or may be removable from arm(s) 52 and may be constructed of any suitable material for use in an operating room, e.g., stainless steel. Surgical tray 60 may be of any shape suitable to retain surgical instruments and other surgical devices thereon and includes an outer peripheral lip 62 to help maintain instruments and/or devices thereon. An underside of surgical tray 60 may have any suitable shape and/or structure to releasably engage arm(s) 52 such that when placed on arm(s) 52, surgical tray 60 is supported in a vertical and horizontal direction. For example, surgical tray 60 may include a plurality of ring supports (not shown) disposed on an underside thereof that are configured to receive arms 52 therein, a plurality of clips (not shown) disposed on an underside thereof that are configured to snap into engagement about arms 52, or any other suitable engagement structure.

Although one configuration of the mechanical features of surgical tray assembly 10 is detailed above, it is envisioned that surgical tray assembly 10 may additionally or alternatively include any other features suitable for use in an operating room and/or facilitating performing one or more surgical procedures.

Referring still to FIGS. 1 and 4, power system 70 of surgical tray assembly 10 is shown. Power system 70 includes electrical cord 80, which may be any suitable electrical cord for use in an operating room. Electrical cord 80 is configured to connect to a standard wall outlet, generator, or other suitable power source. Electrical cord 80 is coupled to surgical tray assembly 10 in electrical cooperation with one or more electrical transmission device(s) 81 disposed on surgical tray assembly 10 for providing power thereto, e.g., from the wall outlet, generator, etc. For exemplary purposes, a plurality of electrical transmission devices 81 are illustrated in FIGS. 1 and 4, although greater or fewer than those shown and/or different types of electrical transmission devices 81 are also contemplated. The electrical transmission device(s) 81 may be any electrical transmission device suitable for use in an operating room, e.g., a physical contact battery charger, a wireless charging apparatus, a standard electrical socket, or the like. One or more cables or wires (not explicitly shown) associated with electrical cord 80, or electrical cord 80 itself, are routed through base member 20 and/or support post 40 to electrically couple electrical cord 80 to the electrical transmission device(s) 81.

With continued reference to FIGS. 1 and 4, one (or more) of the electrical transmission devices 81 may be a physical contact battery charger 83. Physical contact battery charger 83 may define one or more sockets or cavities for receipt of one or more batteries from a battery-powered surgical instrument (not shown). The sockets or cavities of physical contact battery charger 83 are disposed adjacent to or on lip 62 of tray 60 so as not to occupy surface area of tray 60 usable for retaining other surgical instruments, devices, or equipment.

Physical contact battery charger 83 may be integrated into surgical tray assembly 10 and sterilizable therewith, may include various sterilizable interchangeable components each configured to couple to surgical tray assembly 10 for use in charging a particular battery, or may be a stand-alone component (operable independent of surgical tray assembly 10) configured for releasable engagement with surgical tray assembly 10. In the latter-most configuration, physical contact battery 83 may be housed within a cavity or recess of surgical tray assembly 10 with only the sterilizable components thereof exposed. Regardless of the configuration utilized, physical contact battery charger 83 eliminates the need to re-sterilize charged batteries before inserting them back into their respective battery powered surgical instruments and provides a convenient and readily accessible location for charging batteries during the course of a surgical procedure.

Figure 5:
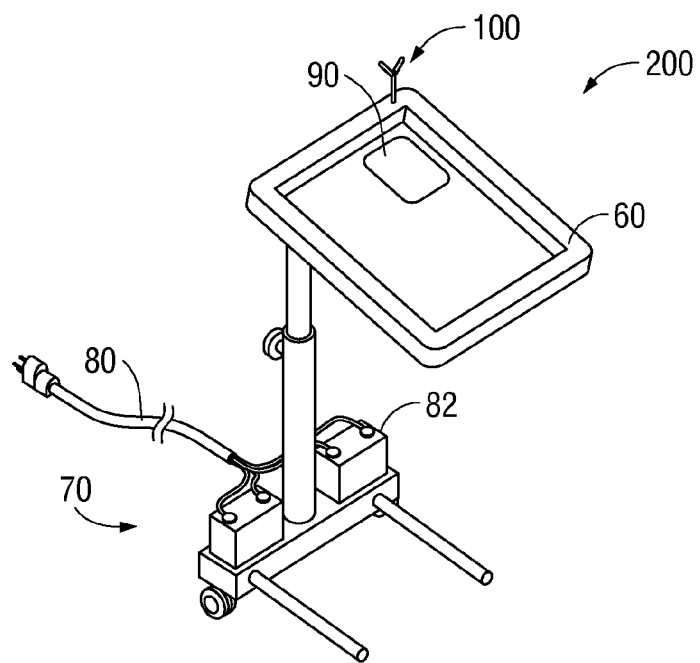
FIG. 5 is a perspective view of another surgical tray assembly provided in accordance with the present disclosure.

Another embodiment of a surgical tray assembly provided in accordance with the present disclosure is illustrated in FIG. 5, generally referred to as surgical tray assembly 200. Surgical tray assembly 200 is similar to surgical tray assembly 10 (FIGS. 1-4), detailed above, and may include any or all of the aspects and features thereof. For purposes of brevity, only differences between surgical tray assembly 200 and surgical tray assembly 100 (FIGS. 1-4) are detailed below.

Surgical tray assembly 200 includes one or more on-board batteries 82 configured to power the electrical components of surgical tray assembly 200. Batteries 82 may be any rechargeable batteries suitable for use in an operating room and having sufficient power and longevity to supply and/or charge battery powered surgical instruments throughout a surgical procedure or number of procedures. Batteries 82 may be in continuous or selective electrical cooperation with electrical cord 80 to enable charging of batteries 82 via electrical cord 80, or may be charged using any other suitable connection(s). Further, batteries 82 may be provided in addition to electrical cord 80 (as shown), or may be provided as an alternative to electrical cord 80. In either configuration, batteries 82 enable use of surgical tray assembly 200 in instances where an external power source is not readily available. Batteries 82 are coupled to the electrical components of surgical tray assembly 200, in addition to or in place of such coupling of electrical cord 80, via routing one or more cables or wires through the base member 20 and/or support post 40 (see FIG. 1) of surgical tray assembly 200, similarly as detailed above.

As illustrated in FIG. 5, two batteries 82 are disposed on elongate body 21, one at each end of elongate body 21; however, other configurations are also contemplated. The positioning of batteries 82 on elongate body 21 facilitates balancing of surgical tray assembly 200 and provides better weight distribution which may be particularly important in instances where larger, heavier batteries 82 are utilized.

With continued reference to FIG. 5, surgical tray assembly 200 includes a wireless charging apparatus 90 disposed on surgical tray 60, although other electrical transmission devices, e.g., physical contact battery charger 83 (FIG. 4) are additionally or alternatively contemplated for use with surgical tray assembly 200. Wireless charging apparatus 90 may be any wireless charging apparatus suitable for charging surgical instruments via wireless charging (e.g., an inductive pad, antenna array, or the like).

Surgical tray assembly 200 further includes a wireless communications system 100 coupled thereto, thus enabling "smart" functionality of surgical tray assembly 200. Wireless communications system 100 may be configured to wirelessly communicate with one or more surgical instruments within range of surgical tray assembly 200, wireless charging apparatus 90 (or any other charging apparatus of surgical tray assembly 200), batteries 82, and/or any other communication-enabled components inside or outside of the operating room. As an alternative to wireless communication with those components mounted on surgical tray assembly 200, e.g., wireless charging apparatus 90 and batteries 82, wired communication between system 100 and such components may be provided.

Wireless communications system 100, more specifically, may be configured to capture data from the one or more surgical instruments or other components in communication therewith. Such data may relate to a plurality of functions and/or parameters, e.g., event log data, usage data, charging/available power data, environmental condition data, fault data, etc. Wireless communication system 100 may be capable of storing and/or transmitting the captured data to one or more servers, computers, and/or other peripheral devices in any suitable fashion (e.g., hard wire, wireless, SD card, or the like).

Figure 6:
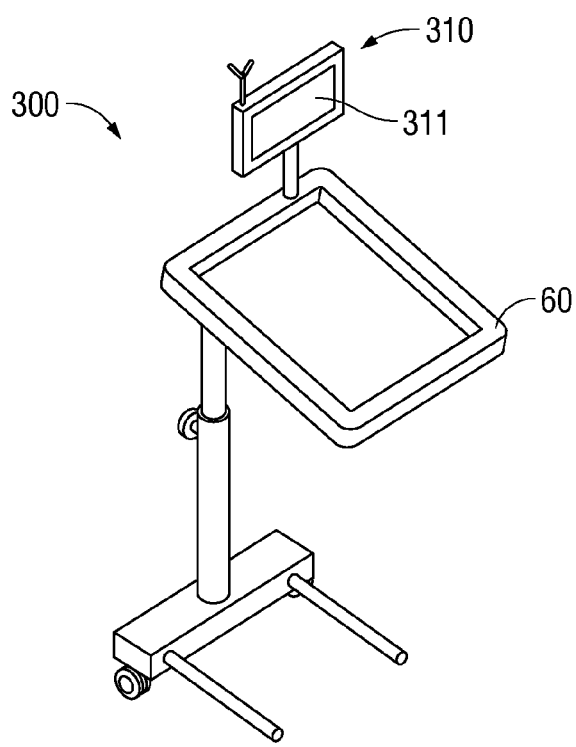
FIG. 6 is a perspective view of another surgical tray assembly provided in accordance with the present disclosure.

Another embodiment of a surgical tray assembly provided in accordance with the present disclosure is illustrated in FIG. 6, generally referred to as surgical tray assembly 300. Surgical tray assembly 300 is similar to surgical tray assembly 10 (FIG. 1) and, thus, only the differences therebetween will be detailed below. Alternatively or additionally, surgical tray assembly 300 may incorporate any or all of the features of surgical tray assembly 200, and vice versa.

Surgical tray assembly 300 includes a user interface display 310 disposed thereon. User interface display 310 is configured to display information relating to the surgical procedure being performed, patient information, information relating to the operation of the surgical instruments utilized (such as parameters, errors, the state of the batteries, and/or alarms), etc. User interface display 310 may be any display suitable for use in an operating room. In one embodiment, user interface display 310 includes a touch screen 311. Touch screen 311 may be any touch screen suitable for use in operating rooms. It is also contemplated that user interface display 310 be configured to communicate (via wired or wireless communication) with surgical instruments, battery chargers, communication systems, and/or other communication-enabled devices associated with or separate from surgical tray assembly 300. More specifically, user interface display 310 may be configured to capture (or receive) data relating to a plurality of functions and/or parameters of the surgical procedure, operating environment, instruments, etc., and to present such data on touch screen 311 for use by the clinician(s). Additionally, user interface display 310 may be capable of transmitting such data to one or more servers, computers, and/or other peripheral devices in any suitable fashion (e.g., hard wire, wireless, SD card, or the like).

It is contemplated that each of the features from the various embodiments of the presently disclosed surgical tray assembly may be utilized with one another in any suitable combination. Therefore, the above description should not be construed as limiting, but merely as exemplifications of embodiments. Those skilled in the art will envision other modifications within the scope and spirit of the present disclosure.

What is claimed is:

1. A surgical tray assembly, comprising:
    a stand;
    a surgical instrument tray supported on the stand;
    an electrical connector coupled to the stand, the electrical connector configured to be inserted into an electrical outlet; and
    at least one electrical transmission device disposed on the surgical instrument tray, wherein the at least one electrical transmission device is in electrical communication with the at least one electrical connector, the at least one electrical transmission device configured to supply power to at least a portion of a surgical instrument disposed on the surgical instrument tray.

2. The surgical tray assembly of claim 1, wherein the stand includes:
    a base member;
    at least one leg extending from the base member;
    at least one caster wheel coupled to the base member;
    at least one support tube extending from an upper side of the base member;
    an elongate body coupled to an upper end of the at least one support tube; and
    at least one tray support extending from a side of the elongate body, wherein the surgical instrument tray is disposed on an upper side of the at least one tray support.

3. The surgical tray assembly of claim 1, further including at least one battery disposed thereon, the at least one battery being in electrical communication with the at least one electrical transmission device.

4. The surgical tray assembly of claim 3, wherein the at least one battery is in electrical communication with the electrical connector.

5. The surgical tray assembly of claim 1, wherein the at least one electrical transmission device is a physical contact battery charger.

6. The surgical tray assembly of claim 1, wherein the at least one electrical transmission device is a wireless charging apparatus.

7. The surgical tray assembly of claim 1, further including a wireless communication system operably coupled to the surgical instrument tray.

8. The surgical tray assembly of claim 7, wherein the wireless communication system is configured to wirelessly communicate with a battery powered surgical instrument and capture data from the battery powered surgical instrument.

9. The surgical tray assembly of claim 1, further including a user interface display disposed on the surgical instrument tray.

10. The surgical tray assembly of claim 9, wherein the user interface display is a touch screen.

11. The surgical tray assembly of claim 9, wherein the user interface display is configured to wirelessly communicate with a battery powered surgical instrument and capture data from the battery powered surgical instrument.

12. The surgical tray assembly of claim 11, wherein the user interface display is configured to display the captured data.

13. A surgical tray assembly, comprising:
    a stand, including:
        a base member;
        an upper member;
        at least one support tube extending between the base member and the upper member; and
        at least one tray support coupled to the upper member;
    a surgical instrument tray supported on the at least one tray support of the stand, the surgical instrument tray including at least one electrical transmission device disposed thereon; and
    an electrical power provider coupled to base member, the electrical power provider being in electrical communication with the at least one electrical transmission device via cables routed through at least one of the base member, the upper member, or the at least one support tube, wherein the electrical power provider is configured to provide power to the at least one electrical transmission device, the at least one electrical transmission device configured to supply power to at least a portion of a surgical instrument disposed on the surgical instrument tray.

14. The surgical tray assembly of claim 13, wherein the power provider is an electrical connector configured to selectively engage a wall outlet thereby causing the electrical connector and wall outlet to be in electrical communication.

15. The surgical tray assembly of claim 13, wherein the power provider is at least one battery seated on the base member.

16. The surgical tray assembly of claim 13, wherein the at least one electrical transmission device is a physical contact battery charger.

17. The surgical tray assembly of claim 13, wherein the at least one electrical transmission device is a wireless charging apparatus.

18. The surgical tray assembly of claim 13, further including a wireless communication system operably coupled to the surgical instrument tray.

19. The surgical tray assembly of claim 18, wherein the wireless communication system is configured to wirelessly communicate with a battery powered surgical instrument and capture data from the battery powered surgical instrument.

20. The surgical tray assembly of claim 13, further including a user interface display disposed on the surgical instrument tray, the user interface display configured to wirelessly communicate with a battery powered surgical instrument and capture and display data received therefrom.

* * * * *